United States Patent
Seng et al.

(10) Patent No.: US 6,253,101 B1
(45) Date of Patent: Jun. 26, 2001

(54) METHOD FOR THE OPERATION OF A DIAGNOSTIC MAGNETIC RESONANCE APPARATUS

(75) Inventors: Gerhard Seng, Herzogenaurach; Wolfgang Risse, Erlangen, both of (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/497,637

(22) Filed: Feb. 3, 2000

(30) Foreign Application Priority Data

Feb. 4, 1999 (DE) .............................. 199 04 537

(51) Int. Cl.$^7$ ............................................ A61B 5/055
(52) U.S. Cl. .................... 600/410; 600/422; 324/309; 324/318
(58) Field of Search .................... 600/410, 415, 600/422; 329/309, 318, 322, 307

(56) References Cited

U.S. PATENT DOCUMENTS

| 4,629,989 | 12/1986 | Riehl et al. ........................ 324/318 |
| 4,924,868 | * 5/1990 | Krause et al. ..................... 600/422 |
| 5,216,367 | * 6/1993 | Mori .................................. 600/422 |
| 5,365,927 | * 11/1994 | Roemer et al. .................... 600/410 |
| 5,722,410 | * 3/1998 | NessAiver .......................... 600/410 |
| 5,936,406 | 8/1999 | Potthast ............................. 324/318 |
| 6,087,831 | * 7/2000 | Bornert et al. .................... 324/307 |

FOREIGN PATENT DOCUMENTS

| 195 08 715 | 9/1996 | (DE) . |
| 0 374 994 | 6/1990 | (EP) . |

* cited by examiner

Primary Examiner—Ruth S. Smith
(74) Attorney, Agent, or Firm—Schiff Hardin & Waite

(57) ABSTRACT

In a method for the operation of a diagnostic magnetic resonance apparatus, a number of local antennas are arranged at known positions with respect to a patient support. Before an activation of at least one of the local antennas for imaging, at least one characteristic property of each local antenna is presented in an overview image of a patient on the patient support. Based on this displayed characteristic property, the optimum local antenna or antennas best suited for obtaining a desired image is/are activated for obtaining image data.

6 Claims, 2 Drawing Sheets

METHOD FOR THE OPERATION OF A DIAGNOSTIC MAGNETIC RESONANCE APPARATUS

BACKGROUND OF THE INVENTION

1. Field of the Invention

The present invention is directed to a method for the operation of a diagnostic magnetic resonance apparatus having a number of local antennas.

2. Description of the Prior Art

In diagnostic magnetic resonance apparatus, local antennas are utilized for improving the signal-to-noise ratio, and thus improving the imaging quality. The positioning of the local antennas applied to a patient in the magnetic resonance apparatus has conventionally ensued with the assistance of a light sighting means, which marks a region that has a defined or known spacing from the magnetic field center or from the center of the imaging region. To that end, a center of the local antenna to be applied is first brought into coincidence with a light indicator generated by the light-sighting means. This can ensue by appropriate placement of the patient on a patient support or by a corresponding positioning of the patient support with the patient thereon. Subsequently, the patient together with the patient support is moved by the defined distance into the imaging region of the magnetic resonance apparatus. In many magnetic resonance apparatuses, the position acquisition is limited to a single coordinate direction, namely the direction of the displacement path of the patient support. It is not possible to communicate the positions of a number of simultaneously employed local antennas to the magnetic resonance apparatus.

German PS 196 53 535, corresponding to U.S. Pat. No. 5,936,406, discloses a method for position determination, wherein spatially-encoded magnetic resonance signals are received with a whole body antenna as well as with the local antennas to be applied. Spatially resolved image information in the form of intensity values are generated from the received magnetic resonance signals. After normalization, the coordinate value that belongs to the highest normalized intensity value is identified, and this indicates the position of the local antenna in the coordinate direction. The position of each local antenna can then be defined and, as needed, communicated to the device controller.

European Application 0 374 994 discloses an antenna system that has a first sub-system in order to generate an overall image and a second sub-system having a number of local antennas. Markers are allocated to the local antennas, these markers being capable of being made visible in an image presentation. The markers allow an identification of the individual local antennas. The antennas allocated to the identified markers can be activated via a control panel. A disadvantage of this system is that the imaged markers are visible in every image and can be disturbing.

SUMMARY OF THE INVENTION

An object of the present invention is to provide a method for facilitating the selection of one or more local antennas that optimally produce an image of the region to be examined.

This object is achieved in a method wherein the local antennas are arranged in known positions with respect to a patient support and preceding activation of at least one of the local antennas for imaging, at least one characteristic property of each local antenna is presented in an overview image of a patient on the patient support. It is thus possible to present an exact allocation of the characteristic property of each local antenna with respect to the patient and to subsequently select a local antenna suitable for the examination. In the actual imaging with the selected local antenna or antennas, the display of the characteristic property can then be turned off (disenabled).

In particular, imaging properties of the antennas employed are provided as characteristic properties. In an embodiment, the sensitive region of each local antenna is graphically presented in correct position as one of the characteristic properties. Which local antenna optimally images the region to be examined is thus shown to the operator in an overview image. In a version of this embodiment, the sensitive region is shown in the form of a bar that is mixed in at one side of the overview image and which has a length corresponding to the expanse of the sensitive region in the direction of the bar. This presentation of the sensitive region indicates the most important information for each applicable local antenna in the overview image, with minimum outlay.

In a further embodiment the local antennas are arranged in fixed position on the patient support, and the position of the support in the magnetic resonance apparatus is taken into consideration for the positionally correct presentation of one of the characteristic properties. The imaged slice with respect to the local antennas is defined via the position acquisition of the patient support.

In another embodiment, the characteristic properties of all local antennas employable for producing resonance images are stored in an antenna data file. The characteristic properties are defined by the antennas themselves. They are determined once and can then be applied to all antennas of the same type.

DESCRIPTION OF THE PREFERRED EMBODIMENTS

Figure 1:
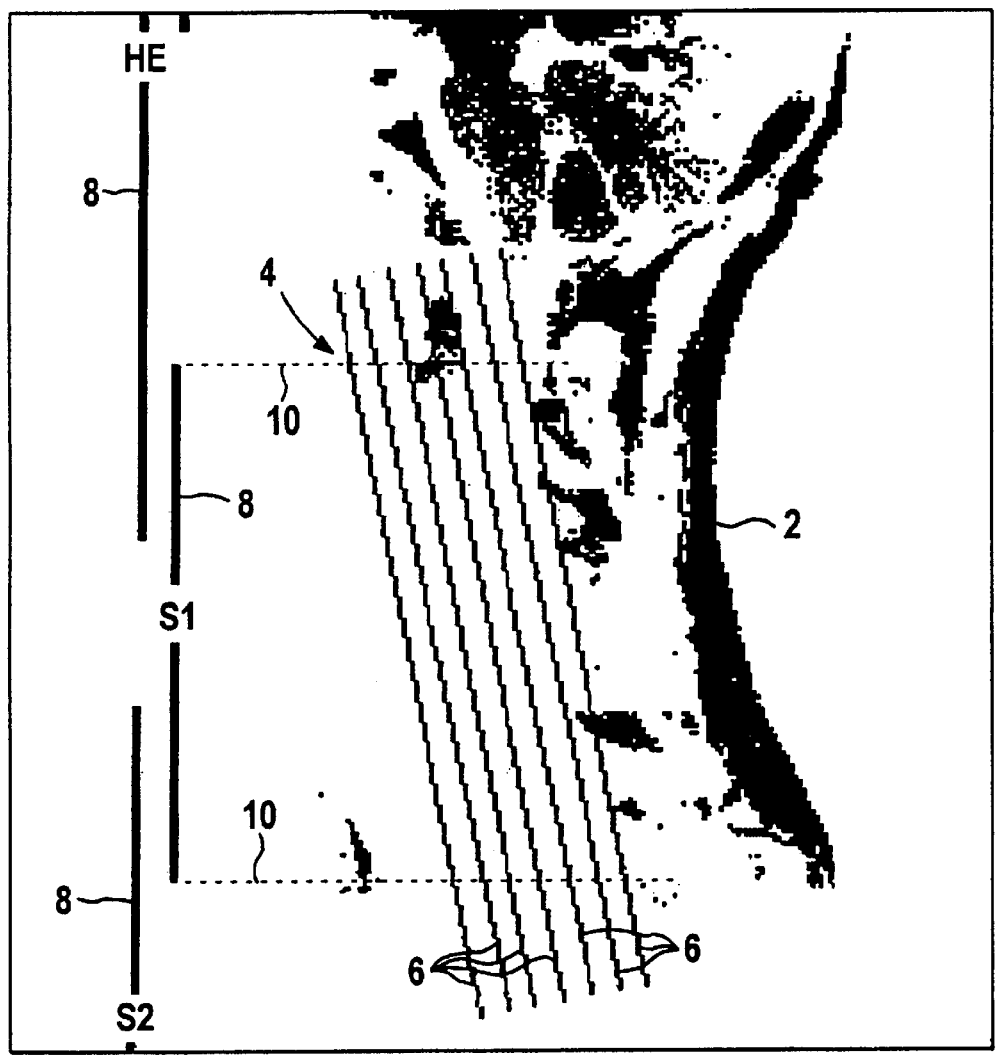
FIG. 1 shows a coarse magnetic resonance overview image wherein the sensitive region of each local antenna is mixed in with a bar in accordance with the inventive method.

FIG. 1 shows an overview image 2 of the head and neck region of a patient in a coarse, black-and-white presentation. The operator has marked a slice group in the overall image 2 that contains seven slices 6 overall, a region to be examined thus can be imaged with high resolution by one or more local antennas. The slices 6 reside perpendicularly to the slice from which the overview image 2 was produced.

Simultaneously with the overall image 2, the sensitive region of the local antennas to be applied is shown by bars 8. In addition to the sensitive region, an abbreviated designation is also mixed in for identification: HE references the head antenna, S1 and S2 respectively reference the elements 1 and 2 of a spine array. The local antennas HE, S1 and S2 are integrated in a patient support (not shown) at fixed and known positions. The sensitive region of the local antennas HE, S1 and S2 extends from the bar 8 toward the examination region in a perpendicular direction. The lateral limits of the sensitive region of the first spine array element S1 are indicated by broken lines 10 only for purposes of explanation and do not actually appear in the overall image 2.

Local antennas HE and/or S1 and/or S2 that are best adapted for imaging the slices 6 can now be distinguished by the operator in the overall image 2. In order to optimally image the slice group 4 shown in FIG. 1, the head antenna HE as well as the first and second elements S1 and S2 of the spine array are to be activated.

The operator can directly implement the selection, however, it is also possible for the selection to be automatically implemented by a control computer which automatically interprets the overview image.

Figure 2:
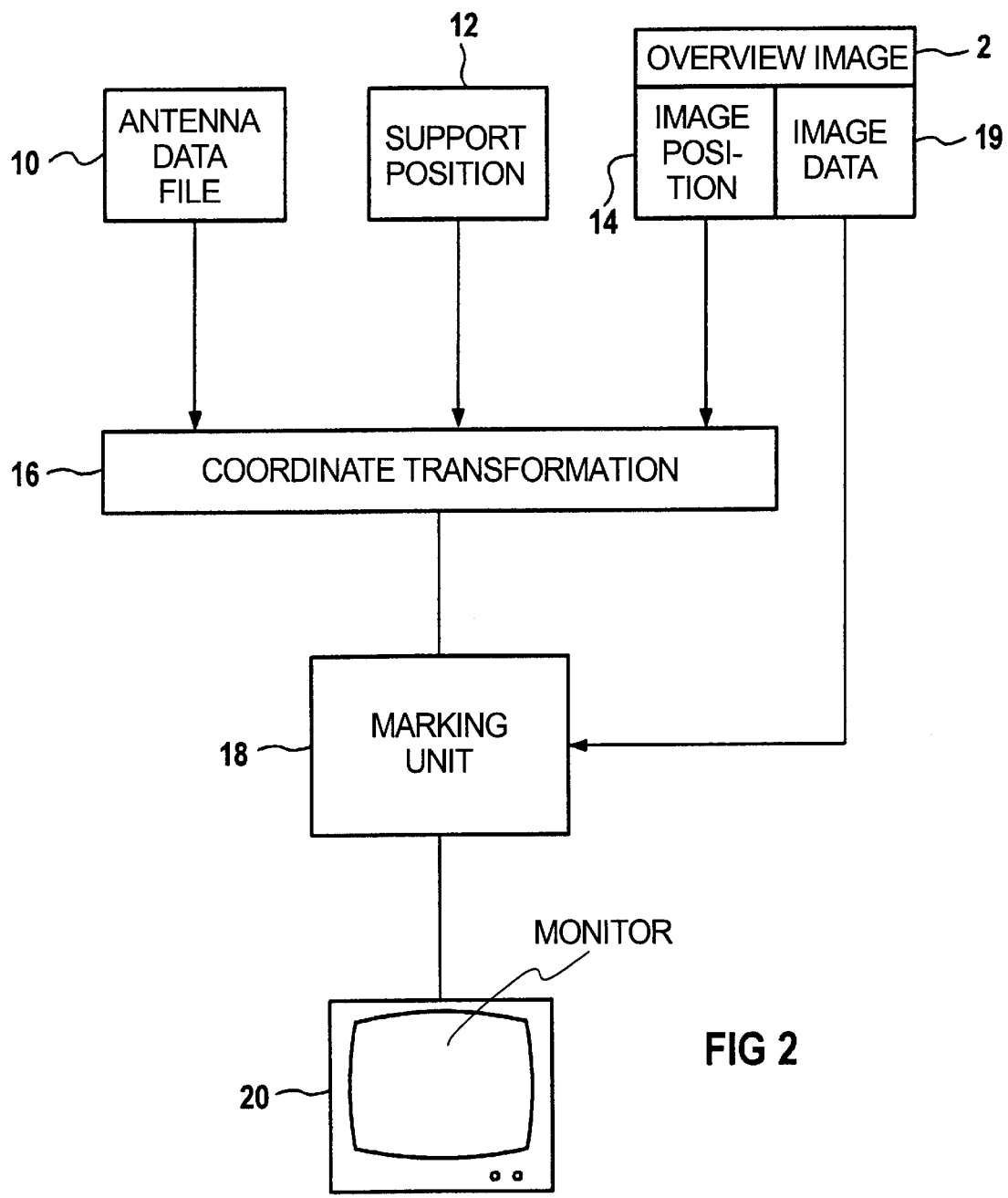
FIG. 2 is a diagram for explaining the inventive method for mixing a characteristic property of each local antenna in an overview image.

In a block diagram, FIG. 2 shows the principal steps for the implementation of the method and their linking to one another. The basic functional units of a diagnostic magnetic resonance apparatus are well-known and are described for example, in Chapter 11 "Magnetresonanztomographie" in the book "Bildgebende Systeme fur die medizinische Diagnostik", edited by Heinz Morneburg, 3rd Edition, 1995. Local antenna information is stored in an antenna data file 10, this information including the position of the local antenna on the patient support as well as the sensitive region of the local antenna. In order to display the characteristic properties of the local antennas in a positionally correct manner in the overview image 2, the antenna positions on the patient support are identified with the assistance of a coordinate transformation 16 dependent on the support position 12 of the patient support in the image position 14 of the overview image. The positionally correct, characteristic antenna properties with respect to the image position 14 are now mixed into image data 19 of the overall image 2 in a marking unit 18 and are then supplied to a monitor 20 for graphic presentation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a diagnostic magnetic resonance apparatus having a plurality of local antennas and a patient support, comprising the steps of:

disposing said local antennas respectively at known positions relative to said patient support;

preceding activation of at least one of said local antennas for obtaining diagnostic image data, displaying at least one characteristic property of each of said local antennas in an overview image of a patient on said patient support;

from said overview image, identifying at least one of said local antennas which is optimum for obtaining said diagnostic image data; and activating said at least one of said local antennas which is optimum for obtaining said diagnostic image data.

2. A method as claimed in claim 1 comprising graphically displaying a sensitive region of each of said local antennas with a correct position relative to said patient in said overview image as said characteristic properties.

3. A method as claimed in claim 2 comprising displaying each of said sensitive regions as a bar mixed at a side of said overview image, with each bar having a length corresponding to a spatial extent of the respective sensitive region of the local antenna, in a direction along said bar.

4. A method as claimed in claim 1 comprising disposing said local antennas at respective fixed positions on said patient support, and using a known position of said support for obtaining the respective positionally correct displays of said characteristic properties of the respective local antennas in said overview image.

5. A method as claimed in claim 1 comprising storing respective characteristic properties for all of said local antennas in an antenna data file, and obtaining said characteristic properties from said antenna data file for local antennas which are available for obtaining selected diagnostic image data in said overview image.

6. A method as claimed in claim 1 comprising automatically determining said at least one of said local antennas which is optimum for obtaining said diagnostic image data, without human intervention.

* * * * *